(12) United States Patent
Hiyama

(10) Patent No.: US 7,144,156 B1
(45) Date of Patent: Dec. 5, 2006

(54) X-RAY DIAGNOSIS APPARATUS

(75) Inventor: Yoichi Hiyama, Sakura (JP)

(73) Assignees: Kabushiki Kaisha Toshiba, Tokyo (JP); Toshiba Medical Systems Corporation, Otawara (JP)

( * ) Notice: Subject to any disclaimer, the term of this patent is extended or adjusted under 35 U.S.C. 154(b) by 0 days.

(21) Appl. No.: 11/413,152

(22) Filed: Apr. 28, 2006

(30) Foreign Application Priority Data

May 13, 2005 (JP) ............................. 2005-141100

(51) Int. Cl.
G03B 42/02 (2006.01)

(52) U.S. Cl. ...................................... 378/167; 378/197

(58) Field of Classification Search ................ 378/167, 378/193–198; 250/370.08, 370.09
See application file for complete search history.

(56) References Cited

U.S. PATENT DOCUMENTS

2001/0036246 A1* 11/2001 Graumann .................... 378/39

* cited by examiner

Primary Examiner—Courtney Thomas
(74) Attorney, Agent, or Firm—Oblon, Spivak, McClelland, Maier & Neustadt, P.C.

(57) ABSTRACT

A driving means for moving a detector in a C-arm includes a first frame including a first pulley, a motor connected to the first pulley, and a first belt stretched over the first pulley, a second frame for supporting the detector, and a third frame provided between the first frame and the second frame. Since the first belt and the third frame are connected to each other by a first connection member, a second pulley and a second belt stretched over the second pulley are mounted, and the second belt is connected to the first frame by a second connection member, an interval between an X-ray tube device and the detector for detecting X-ray becomes wider and a patient can be easily set at a photographing position. In addition, it is possible to lengthen a movement range of the detector to improve a freedom degree of photographing.

4 Claims, 6 Drawing Sheets

X-RAY DIAGNOSIS APPARATUS

BACKGROUND OF THE INVENTION

1. Field of the Invention

The present invention relates to an X-ray diagnosis apparatus using a C-arm type holding device for holding an X-ray source and a detector for detecting X-ray, which face each other, and more particularly, to an X-ray diagnosis apparatus including a driving mechanism for forwardly or backwardly moving a detector relative to an object to be detected, which lies on a top board of a bed.

2. Description of the Related Art

In a clinical field, an X-ray diagnosis apparatus using a C-arm type holding device for holding an X-ray source and a detector for detecting X-ray, which face each other across an object to be detected (patient) on a top board, is known (Japanese Unexamined Patent Application Publication No. 2004-357987). An example of the X-ray diagnosis apparatus is shown in FIGS. 1 and 2.

The X-ray diagnosis apparatus 100 shown in FIG. 1 includes a top board (bed) 101 on which an object to be detected P lies, a C-arm (holding device) 1 for holding an X-ray tube 4 (X-ray source) including an X-ray diaphragm on one side of an object to be detected on the top board 101, and a detector 2 as an image receiving system on the other side thereof, a pedestal (not shown) for movably holding the top board 101 and the C-arm 1, and various operating consoles (not shown) for X-ray photographing.

The X-ray diagnosis apparatus 100 can clinically perform various operations including erection, elevation, forward and backward movement, and left and right movement of the top board 101 relative to the pedestal, longitudinal movement, rotation, and arc movement of the c-arm 1 relative to the pedestal, and forward and backward movement of the detector 1 relative to the top board 101, in order to variously perform necessary positioning.

Among them, as shown in FIG. 2, there is known driving means (driving unit) which forwardly and backwardly moves the detector 2 to and from the object to be detected on the top board 101 relative to the C-arm 1 and drives the detector 2 attached to a belt by a mechanism in which the belt is stretched over a pair of pulley (driving pulley and driven pulley) in a loop shape or a detector 2 attached to a rack by a mechanism using the rack and a pinion.

This mechanism includes a motor 3101 in a first frame 31, a pair of pulleys 3102 and 3102, and a belt 3103 stretched over the pair of pulleys 3102. The motor 3101 is connected to one of the pair of pulleys 3102, and a second frame 32 is connected to the belt 3103 by a connection member 50 such that the detector 2 held by the second frame 32 can move toward the object to be detected P.

However, in the driving means (driving unit 3) employing a one-step slide mechanism using two frames, since the length of the driving unit 3 cannot freely extend by limit of a mounting space, it is difficult to ensure a large movement range of the detector 2.

In other words, when the movement range of the detector is lengthened, the mounting space need become wider and an interval between the X-ray source and the detector becomes narrower. Accordingly, a space for setting the object to be detected (patient) on a photographing position becomes narrower and thus a layout having a difficulty in use is obtained. In contrast, when the interval between the X-ray source and the detector becomes wider, the movement range of the detector becomes narrower and a freedom degree of photographing is reduced.

SUMMARY OF THE INVENTION

An object of the present invention is to provide an X-ray diagnosis apparatus capable of widening an interval between an X-ray tube and a detector to easily set an object to be detected (patient) and lengthening a movement range of the detector to improve a freedom degree of photographing.

According to a first aspect of the present invention, there is provided an X-ray diagnosis apparatus including an arc-shaped arm which includes an X-ray source and a detector, which face each other across an object to be detected on a top board; and a driving means which moves the detector toward the object to be detected to adjust a distance between the X-ray source and the detector, wherein the driving means includes a first frame including a pair of first rotation members provided in parallel to the object to be detected, a driving source for rotating one of the pair of first rotation members, and a first power delivering member which is stretched over the pair of first rotation members and rotates toward the object to be detected, and connected to an end of the arc-shaped arm therein to be protruded, a second frame for supporting the detector, and a third frame slidably provided between the first frame and the second frame, wherein the third frame is connected to the first power delivering member by a first connection member, and includes a pair of second rotation members provided in parallel to the object to be detected and a second power delivering member which is stretched over the pair of second rotation members and rotates toward the object to be detected, and wherein the second power delivering member is connected to the first frame by a second connection member and connected to the second frame by a third connection.

According to the first aspect, since a multi-step slide mechanism including the first to third frames is employed as a driving means (driving unit) and a power delivering structure (first connection member to third connection member) which requires only one driving source is employed, an interval between the X-ray source and the detector can become wider and the object to be detected (patient) can be easily set at a photographing position. In addition, since only one driving source is required, miniaturization and low cost of the apparatus can be accomplished.

According to a second aspect of the present invention, the number of the third frames is plural, and, in adjacent third frames, the second power delivering member mounted in one third frame and the other third frame are connected to each other by a connection member, and the second power delivering member mounted in the other third frame and the one third frame are connected to each other by the connection member.

In the second aspect, since the number of the third frame is plural, the movement amount of the detector can increase.

DETAILED DESCRIPTION OF THE PREFERRED EMBODIMENTS

First Embodiment

An X-ray diagnosis apparatus includes a top board (bed) on which an object to be detected (patient) lies, a C-arm (holding device) as an arc-shaped arm for holding an X-ray tube device (X-ray source) and an X-ray diaphragm on one side of the object to be detected on the top board and holding a flat panel detector (FPD) on the other side thereof, a pedestal for movably holding the top board and C-arm, and a various operating consoles (not shown) for X-ray photographing. Among them, components except the FPD and a driving means (driving unit) for forward and backward movement may employ, for example, those of the above-described conventional example.

Although a pulley is used as an example of a rotation member, a sprocket may be used. In addition, although a belt is used as a power delivering member, a chain or a wire may be used. Furthermore, a motor is used as a driving source (or power source).

Figure 3:
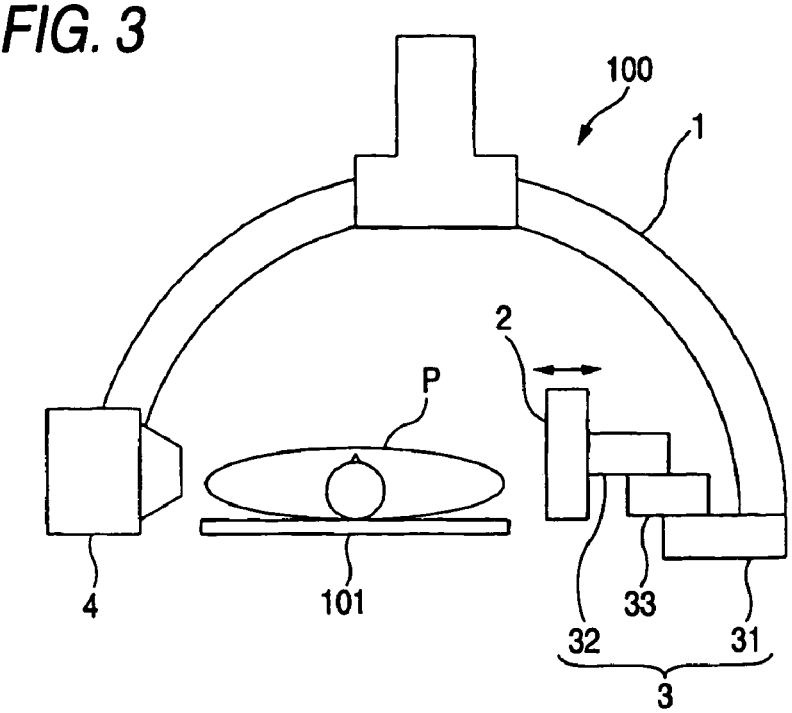
FIG. 3 is a side view showing a main part of an X-ray diagnosis apparatus according to an embodiment of the present invention.
Figure 4:
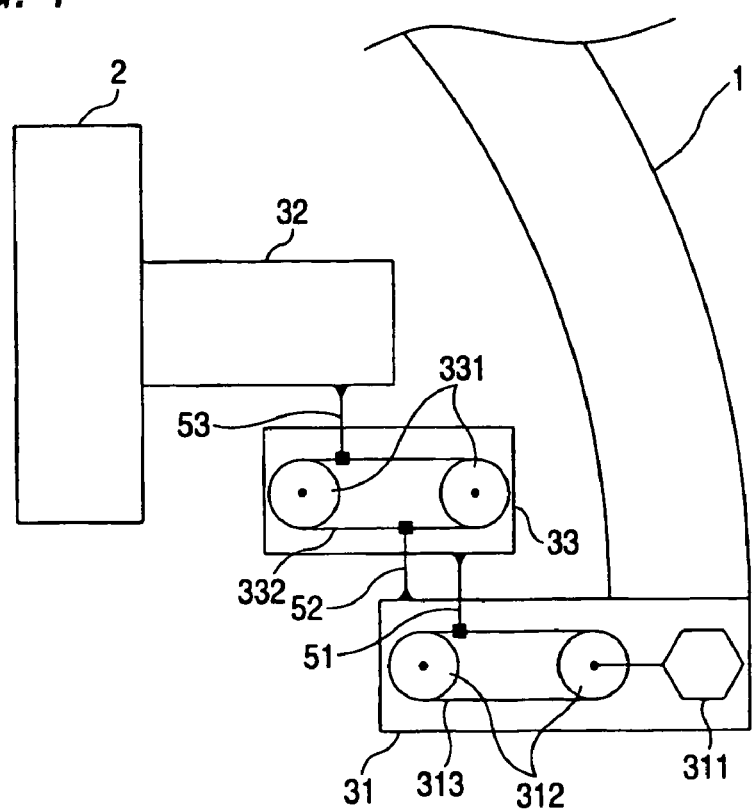
FIG. 4 is a side view showing the main part of the X-ray diagnosis apparatus according to the embodiment of the present invention.

FIG. 3 is a side view showing a main part of the X-ray diagnosis apparatus, that is, a driving unit (driving means) 3 for forwardly and backwardly moving a detector 2 held by the C-arm 1 relative to an object to be detected P who lies on a top board 101. FIG. 4 shows an internal configuration of the driving unit in order to explain a driving mechanism of the X-ray diagnosis apparatus. In the description, a state that frames, which are slidably connected to one another, are separated from one another at a predetermined interval will be shown and described.

As shown in FIG. 3, the X-ray diagnosis apparatus has the driving unit 3 for forwardly and backwardly moving the detector 2. The driving unit 3 includes a first frame 31 having a rectangular parallelepiped shape and supported by the C-arm 1 therein, a third frame 33 having a rectangular parallelepiped shape, which can forwardly and backwardly move relative to the first frame 31 in a predetermined range in the C-arm 1, and a second frame 32 having a rectangular parallelepiped shape, which can forwardly and backwardly move relative to the third frame 33 in a predetermined range in the C-arm 1 and holds the detector 2.

In other words, the third frame 33 is provided between the first frame 31 and the second frame 32 such that the third frame 33 can slide relative to the first frame 31 toward the object to be detected P on the top board 101, and the second frame 32 slides relative to the third frame 33 toward the object to be detected P on the top board 101.

As shown in FIG. 4, in the first frame 31, a motor 311 which is a power source of a movement mechanism moved by the driving unit 3 is mounted.

In addition, in the first frame 31, for example, a pair of two first pulleys 312 and 312 are provided such that axes thereof are arranged in parallel to the object to be detected P on the top board 101 and one first pulley 312 is connected to the motor 311.

In addition, since a first belt 313 is stretched over the pair of the first pulleys 312 and 312, a driving force of the motor 311 rotates the first belt 313 through one first pulley 312 and thus rotates the other first pulley 312. The belt used in the present embodiment is an endless belt and the same is true in the below description.

Figure 1:
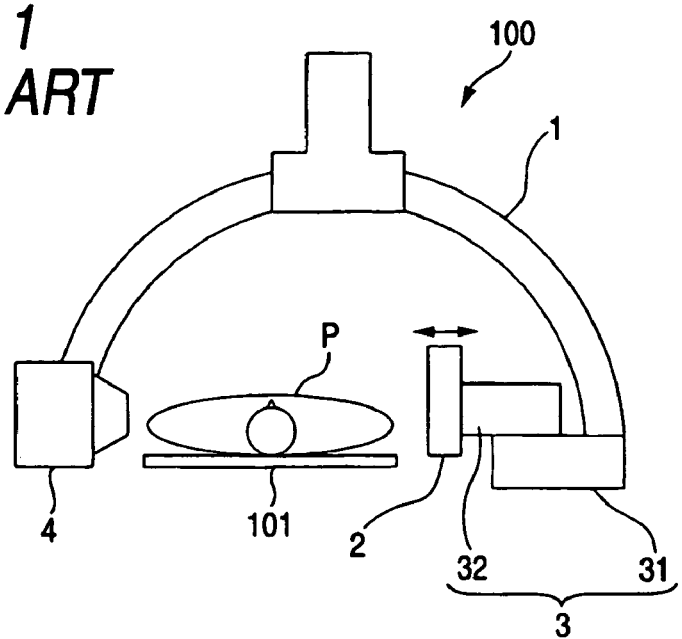
FIG. 1 is a side view showing a main part of a conventional X-ray diagnosis apparatus.
Figure 2:
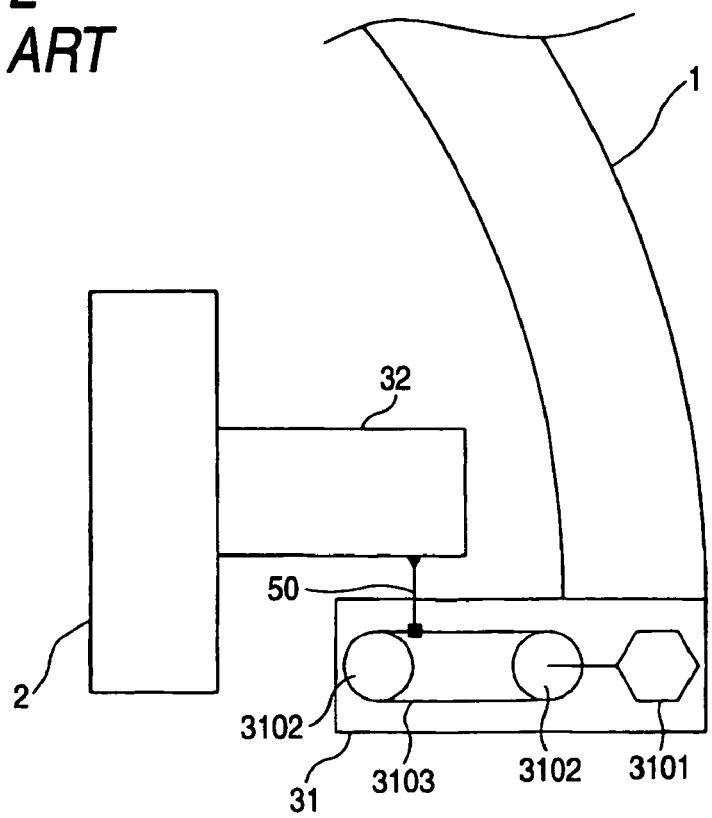
FIG. 2 is a side view showing the main part of the conventional X-ray diagnosis apparatus.

Meanwhile, the motor 311 mounted in the first frame 31 corresponds to the motor 3101 of the conventional X-ray diagnosis apparatus (see FIG. 2), the first pulley 312 corresponds to the pulley 3102, and the first belt 313 corresponds to the belt 3103.

Meanwhile, in the third frame 33 provided between the first frame 31 and the second frame 32, similar to the first frame 31, for example, a pair of two second pulleys 331 and 331 are provided such that axes thereof are arranged in the same direction as that of the object to be detected P on the top board 101, and a second belt 332 is stretched over the pair of the second pulleys 331 and 331. Unlike the first frame 31, a motor for rotating the second pulley 331 is not mounted in the third frame 33.

In addition, the second frame 32 is similar to the second frame 32 of the conventional X-ray diagnosis apparatus (see FIG. 2) in that the second frame 32 holds the detector 2.

The first frame 31, the second frame 32, and the third frame 33 are the above-described configuration. As shown in FIG. 4, a portion close to the third frame 33 in the belt portion between the first pulleys 312 and 312 of the first belt 313 mounted in the first frame 31 is connected to the third frame 33 by a first connection member 51. In other words, the third frame 33 is fixed to be moved by a movement distance of the first belt 313.

In addition, as shown in FIG. 4, a portion close to the first frame 31 in the belt (second belt) 332 stretched over the second pulleys 331 and 331 mounted in the third frame 33 is connected to the first frame 31 by a second connection member 52.

Furthermore, as shown in FIG. 4, a portion close to the second frame 32 in the second belt 332 is connected to the second frame 32 by a third connection member 53. As the connection members 51, 52, and 53, a fastener such as a bolt and a nut provided between the frames and between the frame and the belt is used.

Figure 5A:
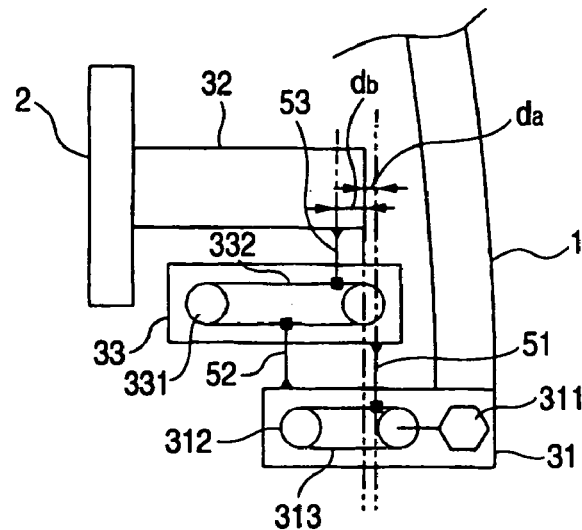
FIGS. 5A, 5B, and 5C are side views showing an operation of a driving unit of the X-ray diagnosis apparatus according to the embodiment of the present invention.
Figure 5B:
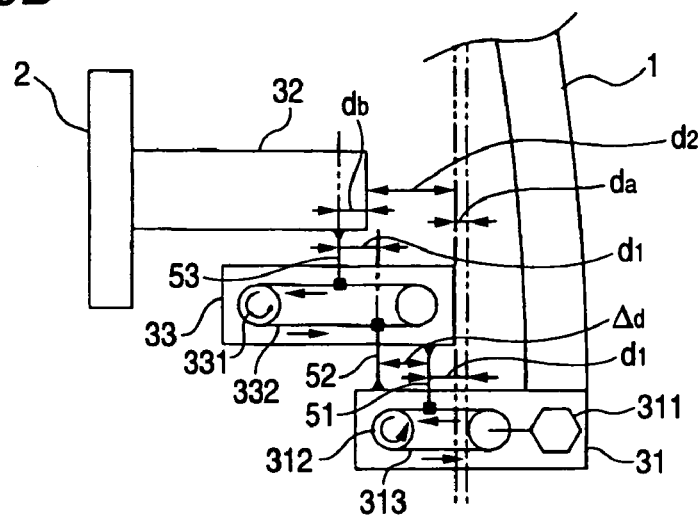
Figure 5C:
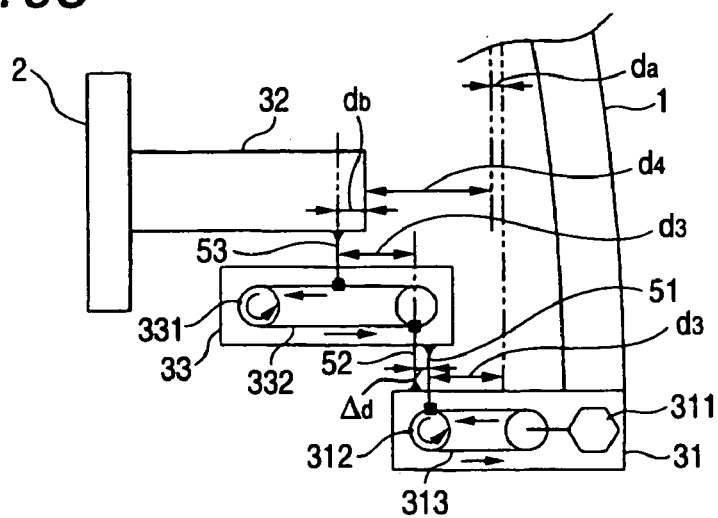

Next, an operation of the X-ray diagnosis apparatus will be described with reference to the attached drawings. FIGS. 5A to 5C show operations of the X-ray diagnosis apparatus, wherein FIG. 5A shows an initial state, FIG. 5B shows a state that the first belt 313 moves by driving the motor 311 such that a displacement of the first belt 313 becomes $d_1$, and FIG. 5C shows a state the first belt 313 moves by driving the motor 311 such that a displacement of the first belt 313 becomes $D_3$.

As shown in FIG. 5A, when the motor 311 mounted in the first frame 31 is driven, the power is delivered to the first pulley 312 attached thereto.

In addition, since one first pulley 312 connected to the motor 311 and the other first pulley 312 form a pair and the first belt 313 is stretched over the first pulley 312 and 312, the first connection member 51 connected to the first belt 313 and the third frame 33 attempts to move the third frame 33 by the same displacement as that of the first belt 313 by delivering the power from the motor 311 to the first belt 313.

Meanwhile, since the second connection member 52 connected between the first frame 31 and the second belt 332 stretched over the pair of the second pulleys 331 and 331 mounted in the third frame 33 delivers a relative movement displacement between the first frame 31 and the third frame 33 and converts the movement displacement into a movement displacement of the second belt 332. Accordingly, the relative movement displacement between the first frame 31 and the third frame 33 generated by delivering the power from the motor 311 to the first belt 313 allows the second belt 332 to be moved by the same displacement as that of the first belt 313 by the second connection member 52.

In addition, since the second belt 332 is also connected to the second frame 32 for holding the detector 2, a relative movement displacement between the first frame 31 and the third frame 33 generated by delivering the power from the motor 311 to the first belt 313 allows the second frame 32 to be moved by the same displacement as that of the second belt 332, which moves by the same displacement as that of first belt 313, by the second connection member 52.

When the motor 311 is driven such that the movement displacement of the first belt 313, for example, becomes $d_1$ in the initial state, as shown in FIG. 5B, the movement displacement of the first belt 313 is converted into the movement displacement of the second belt 332 by the first connection member 51 and the second connection member 52 and the movement displacement of the second belt 332 is converted into the movement displacement of the second frame 32 by the third connection member 53.

Here, when a distance between a rear end of the second frame 32 and the first connection member 51 at the initial state is represented by $d_a$, and a distance between the rear end of the second frame 32 and the third connection member 53 is represented by $d_b$, and, as shown in FIG. 5B, a distance between the first connection member 51 and the second member 52 due to the drive of the motor 311 is represented by $\Delta d$, a relationship between the movement displacement $d_2$ of the second frame 32 and the movement displacement $d_1$ of the third frame 33 (displacement of the first belt 313) satisfies $(d_a+d_b)+d_2=(d_a+d_b)+d_1+\Delta d+d_1$. When $\Delta d=0$, that is, the first connection member 51 and the second connection member 52 are positioned at the same position by driving the motor 311, the movement displacement $d_2$ of the second frame 32 is approximately two times of the movement displacement $d_1$ of the third frame 33.

Similarly, in the state shown in FIG. 5B, when the motor 311 is driven such that the movement displacement of the first belt 313 becomes $d_3$, as shown in FIG. 5C, the movement displacement of the first belt 313 is converted into the movement displacement of the second belt 332 by the first connection member 51 and the second connection member 52 and the movement displacement of the second belt 332 is converted into the movement displacement of the second frame 32 by the connection member 53.

Accordingly, when a horizontal distance between the rear end of the second frame 32 and the mounted position of the first connection member 51 of the first frame 31 at the initial state is represented by $d_a$, and a horizontal distance between the rear end of the second frame 32 and the mounted position of the third connection member 53 in the second frame 32 is represented by $d_b$, and, as shown in FIG. 5B, a distance between the first connection member 51 and the second connection member 52 due to the drive of the motor 311 is represented by $\Delta d$, a relationship between the movement displacement $d_4$ of the second frame 32 and the movement displacement $d_3$ of the third frame 33 (displacement of the first belt 313) satisfies $(d_a+d_b)+d_4=(d_a+d_b)+d_3+\Delta d+d_3$. When $\Delta d=0$, that is, the first connection member 51 and the second connection member 52 are positioned at the same position by driving the motor 311, the movement displacement $d_4$ of the second frame 32 is approximately two times of the movement displacement $d_3$ of the third frame 33.

Since at least three frames (first frame 31, second frame 32, and third frame 33) are connected to one another and moved relative to one another as the driving unit 3 for forwardly and backwardly moving the detector 2 relative to the object to be detected P, and the third frame 33 for delivering the power of the motor 311 mounted in the first frame 31 to the second frame 32 is provided between the first frame 31 connected to an end of the C-arm 1 and the second frame 32 for holding the detector 2, it is possible to increase the movement displacement of the detector 2 twice. Accordingly, since the movement range of the detector can be lengthened, the distance between the detector and the X-ray tube device can become wider when the detector is positioned at an initial position (near the end of the C-arm).

In addition, by mounting the first to third connection members 51 to 53, since one motor 311 mounted in the first frame 31 connected to the end of the C-arm 1 can relatively slide a frame other than the first frame among the three frames for configuring the driving unit 3, only one driving source can be used and thus a cost thereof can be reduced.

Conventionally, the driving unit having at least three frames is not considered. In addition, although the driving unit having at least three frames is considered, it is difficult to derive the structure using the first to third connection members according to the present invention.

Meanwhile, although a mechanism combining the pulley and the belt are described as the driving unit 3 for forwardly and backwardly the detector 2 relative to the object to be detected P, the same effect can be obtained by a combination of a sprocket and a chain or a combination of a pulley and a wire.

Second Embodiment

Next, a second embodiment will be described with reference to FIG. 6. A driving unit 3 for forwardly and backwardly moving a detector 2 relative to an object to be detected P includes at least four frames. In other words, the driving unit 3 includes three frames, that is, a first frame 31 connected to an end of a C-arm 1 and including the motor 311 therein, a second frame 32 for holding the detector 2, and a plurality (two) of third frames 33 provided between the first frame 31 and the second frame 32.

Figure 6:
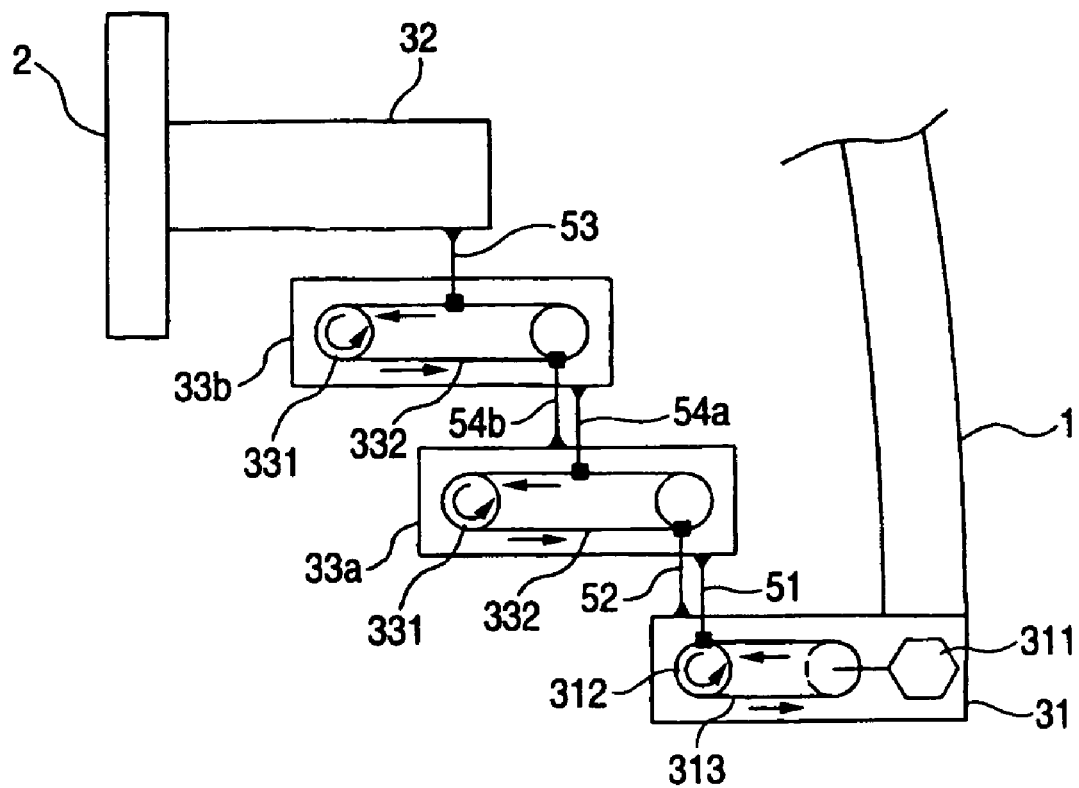
FIG. 6 is a side view showing a driving unit of an X-ray diagnosis apparatus according to another embodiment of the present invention.

As shown in FIG. 6, the driving unit 3 includes the first frame 31 having a rectangular parallelepiped shape and supported by the C-arm 1 therein, the plurality of third frame 33a and 33b having a rectangular parallelepiped shape, which can forwardly and backwardly move relative to the first frame 31 in a predetermined range in the C-arm 1, and the second frame 32 having a rectangular parallelepiped shape, which can forwardly and backwardly move relative to the third frames 33a and 33b in a predetermined range in the C-arm 1 and holds the detector 2.

In other words, the plurality of third frames 33a and 33b are provided between the first frame 31 and the second frame 32 such that one third frame 33a adjacent to the first frame 31 can slide relative to the first frame 31 toward an object to be detected P on a top board 101, and the other third frame 33b adjacent to the second frame 32 can slide relative to the second frame 32 toward the object to be detected P on the top board 101, and the third frame 33a and the third frame 33b slide relative to each other toward the object to be detected P on the top board 101.

In addition, in the first frame 31, a motor 311 which is a power source of a movement mechanism moved by the driving unit 3 is mounted.

In addition, in the first frame 31, for example, a pair of two first pulleys 312 and 312 are provided such that axes thereof are fixed at a predetermined interval in the same direction as that of the object to be detected P on the top board 101 and one first pulley 312 is connected to the motor 311.

In addition, since a first belt 313 is stretched over the first pulleys 312 and 312, a driving force of the motor 311 rotates the first belt 313 through one first pulley 312 and then rotates the other first pulley 312.

Meanwhile, the motor 311 mounted in the first frame 31 corresponds to the motor 3101 of the conventional X-ray diagnosis apparatus (see FIG. 2), the first pulley 312 corresponds to the pulley 3102, and the first belt 313 corresponds to the belt 3103.

Meanwhile, in each of the third frames 33a and 33b provided between the first frame 31 and the second frame 32, similar to the first frame 31, for example, a pair of two second pulleys 331 and 331 are provided such that axes thereof are fixed at a predetermined interval in the same direction as that of the object to be detected P on the top board 101, and a second belt 332 is stretched over the pair of the second pulleys 331 and 331. Unlike the first frame 31, a motor for rotating the second pulley 331 is not mounted in the third frames 33a and 33b.

The second frame 32 is similar to the second frame 32 of the conventional X-ray diagnosis apparatus (see FIG. 2) in that the second frame 32 holds the detector 2.

The first frame 31, the second frame 32, and the third frames 33a and 33b have the above-described configuration, and the first belt 313 mounted in the first frame 31 is connected to the adjacent third frame 33a by a first connection member 51.

In addition, the second belt 332 mounted in the third frame 33a (third frame 33a adjacent to the first frame 31) connected to the first connection member 51 is connected to the first frame 31 by a second connection frame 52, similar to the above-described embodiment.

In addition, the second belt 332 mounted in the third frame 33b (third frame 33b interposed between the second frame 32 and the third frame 33a when the driving unit 3 includes four frames) adjacent to the second frame 32 is connected to the second frame 32 by a third connection member 53.

In addition, the second belt 332 mounted in the third frame 33a is connected to the third frame 33b by a fourth connection member 54a on the opposite side of the second connection member 52, and the second belt 332 mounted in the third frame 33b is connected to the third frame 33a by a fifth connection member 54b on the opposite side of the third connection member 53.

In other words, in the plurality of third frames 33 provided between the first frame 31 and the second frame 32, the second belt mounted in one of adjacent the third frame 33 (third frame 33a) and the other of third frames (third frame 33b) are connected to each other by the fourth connection member 54a and the second belt mounted in the other of the third frames (third frame 33b) and one of the third frames (third frame 33a) are connected to each other by the fifth connection member 54b.

Figure 7A:
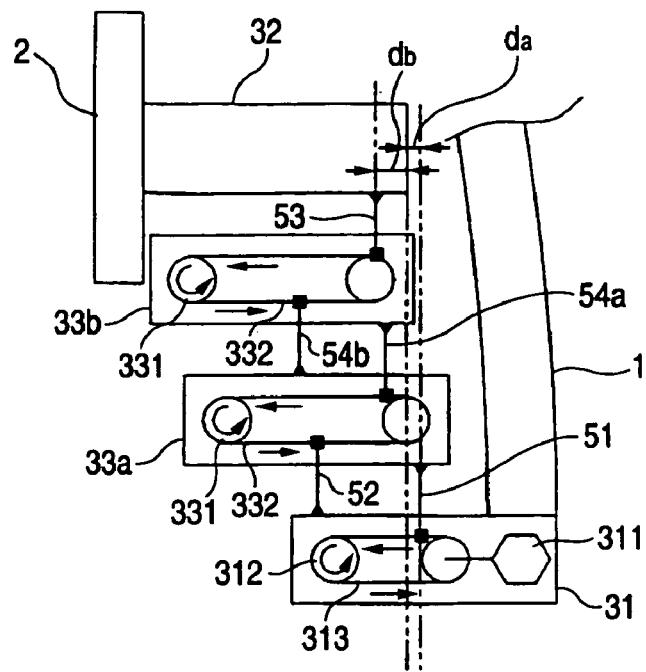
FIGS. 7A and 7B are side views showing an operation of the driving unit of the X-ray diagnosis apparatus according to the embodiment of the present invention.
Figure 7B:
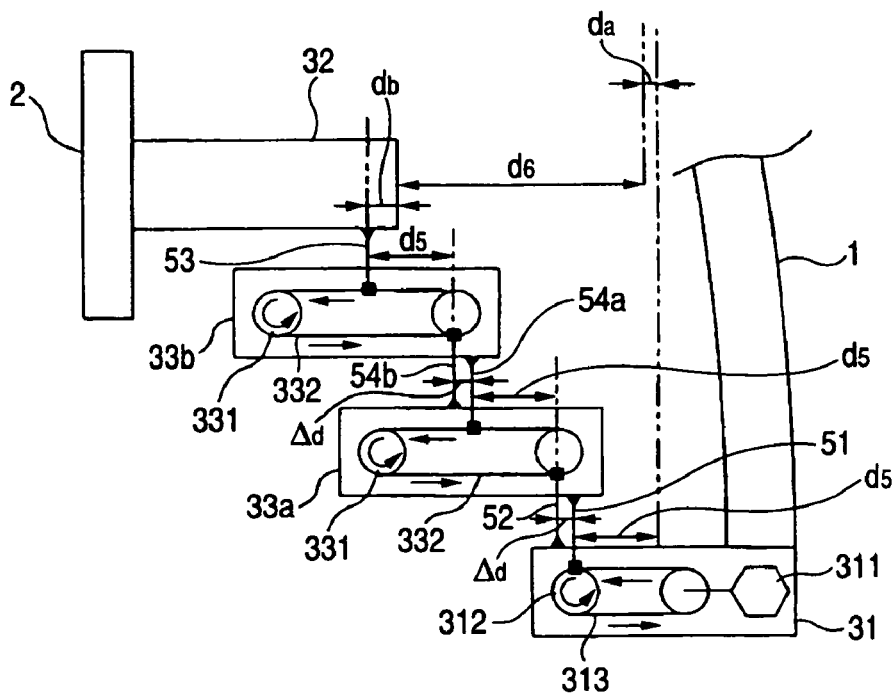

Next, an operation of the X-ray diagnosis apparatus according to the present invention will be described with reference to FIGS. 7A and 7B. FIG. 7A shows an initial state and FIG. 7B shows a state that the first belt 313 moves such that a displacement of the first belt 313 becomes $d_6$.

As shown in FIG. 7A, the motor 311 mounted in the first frame 31 is driven such that the power is delivered to the first pulley 312 attached thereto.

In addition, since one first pulley 312 connected to the motor 311 and the other first pulley 312 form a pair and the first belt 313 is stretched over the first pulleys 312 and 312, the first connection member 51 connected to the first belt 313 and the third frame 33a attempts to move the third frame 33a by the same displacement as that of the first belt 313 by delivering the power from the motor 311 to the first belt 313.

Meanwhile, since the second connection member 52 connected between the first frame 31 and the second belt 332 stretched over the pair of the second pulleys 331 and 331 mounted in the third frame 33a delivers a relative movement displacement between the first frame 31 and the third frame 33a and converts the movement displacement into a movement displacement of the second belt 332. Accordingly, a relative movement displacement between the first frame 31 and the third frame 33a generated by delivering the power from the motor 311 to the first belt 313 allows the second belt 332 to be moved by the same displacement as that of the first belt 313 by the second connection member 52.

In addition, since the second belt 332 mounted in the third frame 33a is connected to the adjacent third frame 33b by the fourth connection member 54a, a relative movement displacement between the first frame 31 and the third frame 33a generated by delivering the power from the motor 311 to the first belt 313 allows the third frame 33b to be moved by the same displacement as that of the second belt 332, which moves by the same displacement as that of the first belt 313, by the fourth connection member 54a. In addition, since, in the third frame 33b connected to the second belt 332 mounted in the third frame 33a by the fourth connection member 54a, the second belt 332 stretched over the second pulleys 331 and 331 mounted therein is connected to the third frame 33a by the fifth connection member 54b, the power delivered from the motor 331 allows the second belt 332 mounted in the third frame 33b to be moved by the same displacement as that of the first belt 313 (second belt 332 mounted in the third frame 33a) through the second belt 332 mounted in the third frame 33a and the first belt 313.

In addition, the second belt 332 mounted in the third frame 33b is also connected to the second frame 32 for holding the detector 2, the relative movement displacement between the first frame 31 and the third frames 33a and 33b generated by delivering the power from the motor 311 to the first belt 313 allows the second frame 32 to be moved by the same displacement as that of the second belts 332 and 332, which move by the same displacement as that of the first belt 313, by the third connection member 53.

When the motor 311 is driven such that the movement displacement of the first belt 313, for example, becomes $d_6$ in the initial state, as shown in FIG. 7B, the movement displacement of the first belt 313 is converted into the movement displacement of the second belt 332 mounted in the third frame 33a by the first connection member 51 and the second connection member 52, the movement displacement of the second belt 332 mounted in the third frame 33a is converted into the movement displacement of the second belt 332 mounted in the third frame 33b by the fourth connection member 54a and the fifth connection member 54b, and the movement displacement of the second belt 332 mounted in the third frame 33b is converted into the movement displacement of the second frame 32 by the third connection member 53.

Accordingly, when a horizontal distance between a rear end of the second frame 32 and the mounted position of the first connection member 51 in the first frame 31 at the initial state is represented by $d_a$, and a horizontal distance between the rear end of the second frame 32 and the mounted position of the third connection member 53 in the second frame 32 at the initial state is represented by $d_b$, and a horizontal distance between the first connection member 51 and the second connection member 52 (horizontal distance between the fourth connection member 54a and the fifth connection member 54b) due to the drive of the motor 311 is represented by $\Delta d$, a relationship between the movement displacement $d_6$ of the second frame 32 and the movement displacement $d_5$ of the third frame 33a (or 33b) (displacement of the first belt 313) satisfies $d_a+d_6+d_b=d_5+\Delta d+d_5+\Delta d+d_5$. When $\Delta d=0$, that is, the first connection member 51 and the second connection member 52 are positioned at the same position by driving the motor 311, the movement displacement $d_6$ of the second frame 32 is approximately three times of the movement displacement $d_5$ of the third frame 33.

Since at least four frames (first frame 31, second frame 32, and third frames 33a and 33b) are connected to one another and moved relative to one another as the driving unit 3 for forwardly and backwardly moving the detector 2 relative to the object to be detected P, it is possible to increase the movement displacement of the detector 2 by increasing the number of the frames.

In addition, by mounting the first to fifth connection members 51 to 54, since one motor 311 mounted in the first frame 31 connected to the end of the C-arm 1 can relatively slide a frame other than the first frame among at least three frames for configuring the driving unit 3, only one driving source can be used and thus a cost thereof can be reduced.

Meanwhile, although a mechanism combining the pulley and the belt is described as the driving unit 3 for forwardly and backwardly moving the detector 2 relative to the object to be detected P, the same effect can be obtained by a combination of a sprocket and a chain or a combination of a pulley and a wire.

In addition, by adjusting the length of the first belt 313 or the second belt 332, a distance between the pairs of pulleys (312 and 331) mounted in the first frame 31 and the third frame 32, connection positions of the respective frames and the respective belts of the first connection member 51, the second connection member 52, the third connection member 53, and the fourth connection member 54, and the forward and backward movement displacement of the detector 2 can be controlled.

In addition, although, in the above-described embodiment, the third frame 33 and the second frame 32 are sequentially connected to the first frame 31 connected to the end of the C-arm 1 to be laminated in the C-arm 1, a connection direction of at least a portion thereof may be, if necessary, a direction perpendicular to a curvature surface of the C-arm 1. For example, there is an aspect that the connection directions of all the frames 31 to 33 are perpendicular to the connection direction of each frame in the above-described embodiment or an aspect that the connection direction between the first frame 31 and the third frame 33 and the connection direction between the second frame 32 and the third frame 33 are perpendicular to each other. By this configuration, since the limit of the area in the C-arm 1 is solved, the present invention is applicable to a case where the length or the number of the frames increases.

Third Embodiment

Figure 8:
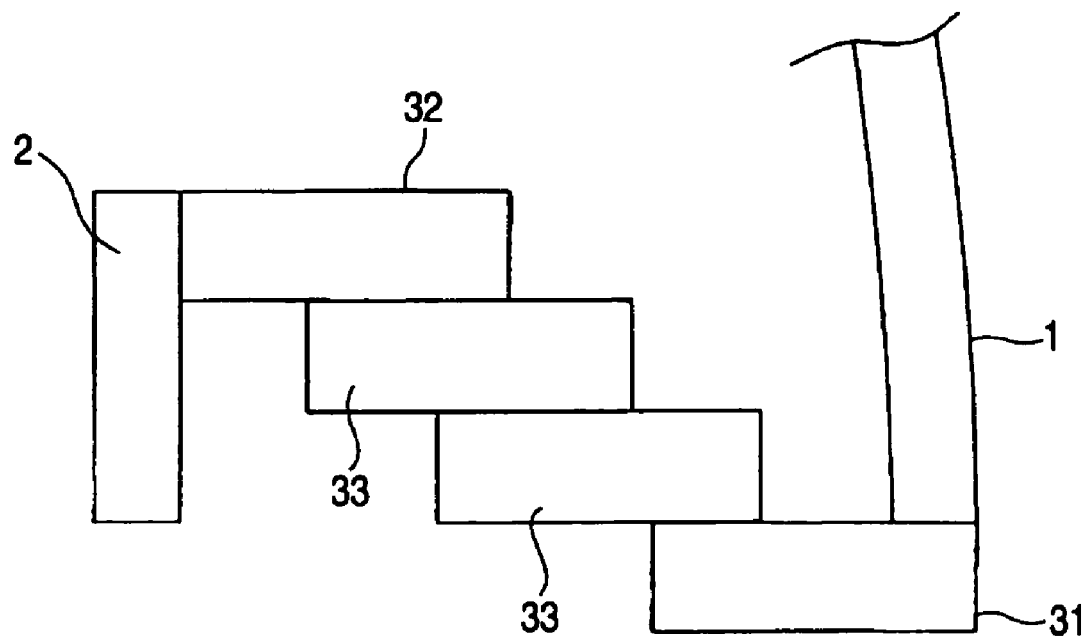
FIG. 8 shows another embodiment of the present invention.

In addition, when the number of the frames increases to three or four, the height of the mechanism increases and a position for holding a detector is shifted upward. However, this problem can be solved by attaching the detector 2 at a position lower than an uppermost frame 32, as shown in FIG. 8.

What is claimed is:

1. An X-ray diagnosis apparatus comprising:
an arc-shaped arm which includes an X-ray source and a detector, which face each other across an object to be detected on a top board; and
a driving means which moves the detector toward the object to be detected to adjust a distance between the X-ray source and the detector,
wherein the driving means includes
a first frame including a pair of first rotation members provided in parallel to the object to be detected, a driving source for rotating one of the pair of first rotation members, and a first power delivering member which is stretched over the pair of first rotation members and rotates toward the object to be detected, and connected to an end of the arc-shaped arm therein to be protruded,
a second frame for supporting the detector, and
a third frame slidably provided between the first frame and the second frame,
wherein the third frame is connected to the first power delivering member by a first connection member, and includes a pair of second rotation members provided in parallel to the object to be detected and a second power delivering member which is stretched over the pair of second rotation members and rotates toward the object to be detected, and
wherein the second power delivering member is connected to the first frame by a second connection member and connected to the second frame by a third connection.

2. The X-ray diagnosis apparatus according to claim 1, wherein the number of the third frames is plural, and, in adjacent third frames, the second power delivering member mounted in one third frame and the other third frame are connected to each other by a connection member, and the second power delivering member mounted in the other third frame and the one third frame are connected to each other by the connection member.

3. The X-ray diagnosis apparatus according to claim 1, wherein the pair of rotation members is a pair of pulleys, and the power delivering member is a belt stretched over the pair of pulleys.

4. The X-ray diagnosis apparatus according to claim 1, wherein the pair of the rotation members is a pair of sprockets, and the power delivering member is a chain stretched over the pair of sprockets.

* * * * *